(12) United States Patent
McWhirter et al.

(10) Patent No.: US 6,896,384 B2
(45) Date of Patent: May 24, 2005

(54) LASER BEAM TRANSLATION SYSTEM AND METHOD

(75) Inventors: John E. McWhirter, Orlando, FL (US); David Eskew, Orlando, FL (US); David Thair, Orlando, FL (US)

(73) Assignee: Alcon RefractiveHorizons, Inc., Fort Worth, TX (US)

( * ) Notice: Subject to any disclaimer, the term of this patent is extended or adjusted under 35 U.S.C. 154(b) by 98 days.

(21) Appl. No.: 10/463,839

(22) Filed: Jun. 17, 2003

(65) Prior Publication Data

US 2004/0264012 A1 Dec. 30, 2004

(51) Int. Cl.⁷ .............................................. G02B 7/182
(52) U.S. Cl. ........................ 359/872; 359/198; 403/291
(58) Field of Search ................................ 359/198, 811, 359/819, 822, 871, 872, 877; 248/476, 479, 486; 403/24, 291

(56) References Cited

U.S. PATENT DOCUMENTS

| | | | |
|---|---|---|---|
| 3,807,029 A | | 4/1974 | Troeger |
| 3,811,665 A | | 5/1974 | Seelig |
| 3,813,089 A | | 5/1974 | Troeger |
| 3,825,992 A | | 7/1974 | Troeger |
| 4,327,527 A | | 5/1982 | Seelig et al. |
| 4,405,184 A | | 9/1983 | Bahiman |
| 4,802,784 A | | 2/1989 | Brooks |
| 4,812,072 A | | 3/1989 | Brooks |
| 5,061,107 A | | 10/1991 | Brooks |
| 5,102,255 A | * | 4/1992 | Heinz .......................... 403/291 |
| 5,160,112 A | * | 11/1992 | Pritchard et al. ........... 248/604 |
| 5,520,679 A | | 5/1996 | Lin |
| 5,550,669 A | * | 8/1996 | Patel .......................... 359/224 |
| 6,678,443 B2 | * | 1/2004 | Engelhardt ................... 385/25 |

OTHER PUBLICATIONS

Troeger et al., "Considerations in the Application of Flexural Pivots," Automatic Control Data Systems Engineering, vol. 17, No. 4, Nov. 1962.
Free–Flex Pivot Frictionless Bearing. Product Brochure, TRW Aeronautical Systems Lucas Aerospace, pp. 10.
Free–Flex Flexural Pivot Engineering Data. Product Brochure, TRW Aeronautical Systems Lucas Aerospace. pp. 16.
C–Flex, The Bearing Solution. Product Brochure, C–Flex Bearing Co., Inc. pp. 6.
Suggested Methods of Mounting Free–Flex Pivots. Product Brochure. TRW Aeronautical Systems Lucas Aerospace. pp. 8.

* cited by examiner

*Primary Examiner*—Mark A. Robinson
(74) *Attorney, Agent, or Firm*—Allen, Dyer, Doppelt, Milbrath & Gilchrist, P.A.

(57) ABSTRACT

A light-translation system includes a fixed base and translatable mirror mount having mirror-supporting brackets. A first and second arm are pivotally attached in parallel, spaced-apart relation adjacent first ends to the base and adjacent second ends to the mirror mount to form a parallelogram-shaped attachment with the base and mirror mount. The pivotal attachments are formed using flexural pivots, each having a thick portion oriented for achieving minimal angular deviation of the mirror. A first bracket has three pads for supporting one side of the mirror. A second bracket has two surfaces shaped to support an edge of the mirror, each surface positioned opposite a pad. A washer dimensioned to admit a mounting screw is positionable opposite a third pad against an outside wall of the mirror mount to removably retain the mirror without imposing appreciable bending stress thereon.

12 Claims, 11 Drawing Sheets

LASER BEAM TRANSLATION SYSTEM AND METHOD

FIELD OF THE INVENTION

The invention relates generally to laser systems, and more particularly to a laser system used to erode a surface such as an eye's corneal tissue.

BACKGROUND OF THE INVENTION

Methods for scanning a laser beam on a workpiece's surface is known in the art. In the field of ophthalmic medicine, for example, photorefractive keratectomy (PRK) is a procedure for laser correction of focusing deficiencies of the eye by modification of corneal curvature, generally accomplished by use of a 193-nanometer wavelength excimer laser beam that ablates away the workpiece, i.e., corneal tissue, in a photodecomposition process. An example of devices known in the art includes that described in commonly owned U.S. Pat. No. 5,980,513.

Once an ablation pattern is determined for a particular eye, the laser beam must be moved quickly and accurately. It is also desirable that the laser beam shots remain parallel to each other when the beam is translated in an X-Y plane. Further, since laser beam motion is typically achieved using mirrors, which must be replaced at certain intervals, it is desirable that a laser translation system have components that are easily and quickly replaceable, most desirably in the field. In addition, it is desirable that such components, when replaced, remain aligned in the field and retain alignment during use.

It is known to use flexural pivots in a parallelogram shape to maintain mirror optics in a perpendicular configuration relative to a surface for achieving lateral motion. However, in previously used systems, the center shift experienced by the pivots during flexion has created an undesirable angular deviation sufficient to obviate the use of such pivots in a laser scanning application requiring the level of accuracy in the ophthalmic arena.

SUMMARY OF THE INVENTION

In accordance with the present invention, an eye treatment laser beam delivery system is provided. A treatment laser and its projection optics generate laser light along an original beam path (i.e., the optical axis of the system) at an energy level suitable for treating the eye. An optical translator shifts the original beam path in accordance with a specific scanning pattern so that the original beam is shifted onto a resulting beam path that is parallel to the original beam path. An optical angle adjuster changes the resulting beam path's angle relative to the original beam path such that the laser light is incident on the eye.

In the present invention, the optical translator comprises a system for translating incoming laser light in at least one direction with great precision and accuracy. The light beam translation system comprises a fixed base and a translatable mirror mount having means for affixing a mirror thereto.

A first and a second arm are pivotally attached in generally parallel, spaced-apart relation to the base and the mirror mount. The arms are attached adjacent first ends to the base and adjacent second ends to the mirror mount, the first and the second arms thereby forming a generally parallelogram-shaped attachment element with the base and the mirror mount.

The pivotal attachments are formed using four flexural pivots. Each flexural pivot has a thick portion that is oriented for achieving optimal stability by minimizing runout, preferably by orienting pairs of pivots to cancel out the deviation caused by the pivots' center shift when undergoing rotation. A first and a second flexural pivot are positioned at a junction between the first ends of the first and the second arm and the base so that the thick portions of a front section thereof are oriented along an outer arc of the pivot. A third and a fourth flexural pivot are positioned at a junction between the second ends of the first and the second arm and the mirror mount so that the thick portions of a front section thereof are oriented along a top arc of the pivot.

Means are also provided for translating the mirror mount in a plane.

Another aspect of the invention is directed to the mirror affixing means, which includes a first and a second bracket affixed to the mirror mount. The first bracket has three generally coplanar pads thereon for supporting a reflective side of the mirror thereagainst. A second bracket has two surfaces shaped to support an edge of the mirror thereagainst opposed to the reflective side. Each of the two surfaces is positioned generally opposite a respective first and a second one of the pads.

A removable mounting screw extends through the mirror mount. A washer is dimensioned to admit the mounting screw and is positionable generally opposite a third pad against an outside wall of the housing. The washer is also positionable to retain the mirror in contact with the pads and the surfaces in a predetermined orientation, the pads, the surfaces, and the washer thereby operable to removably retain the mirror within the housing without imposing bending stress on the mirror sufficient to cause the reflective surface to substantially depart from planarity.

DETAILED DESCRIPTION OF THE INVENTION

A preferred embodiment of the present invention will now be presented with reference to FIGS. 1–10.

An exemplary laser beam delivery and eye tracking system 90 (FIG. 1) may comprise, for example, that taught in U.S. Pat. No. 5,980,513, co-owned with the present application, the contents of which are incorporated herein by reference. The laser beam delivery portion of system includes treatment laser source 91, projection optics 92, X-Y translation mirror optics 10, beam translation controller 93, dichroic beamsplitter 94, and beam angle adjustment mirror optics 95. The laser pulses are distributed as shots over the area to be ablated or eroded, preferably in a distributed sequence so that the desired shape of the object or cornea is achieved. Preferably the pulsed laser beam is shifted to direct the shots to a plurality of spatially displaced positions on the corneal surface to form a plurality of spatially distributed ablation spots. Each of these spots may have a predetermined diameter, for example, 2.5 or 1.0 mm, and may have an intensity distribution, for example, defined by a Gaussian or a generally flat distribution profile across the spot.

Figure 1:
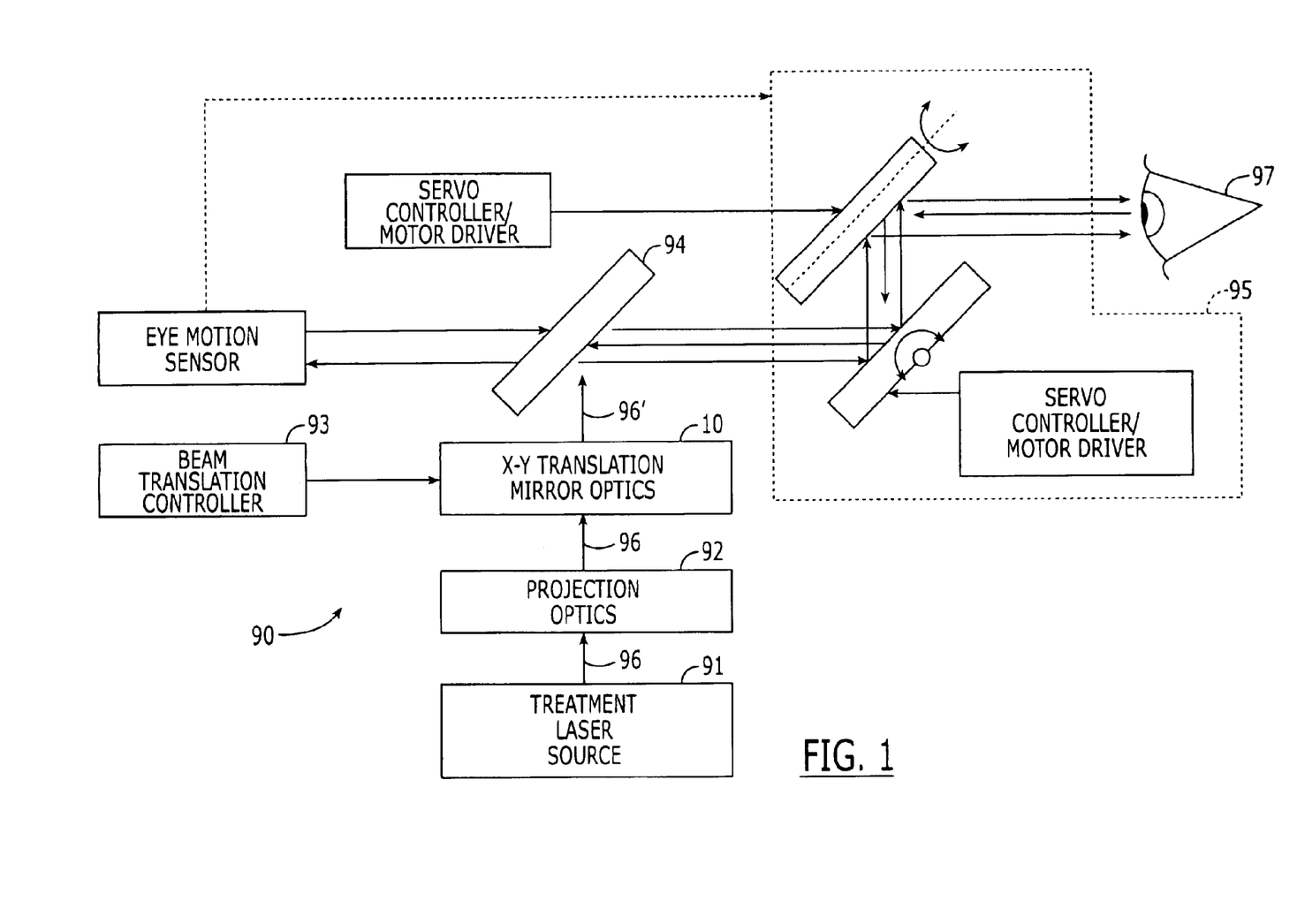
FIG. 1 is a sectional view of the projection optics used with the ophthalmic treatment laser embodiment of the laser beam delivery portion of the present invention.

In operation of the beam delivery portion of system 90, laser source 91 produces laser beam 96 incident upon the projection optics 92. Projection optics 92 adjusts the diameter and distance to focus of beam 96 depending on the requirements of the particular procedure being performed.

After exiting projection optics 92, beam 96 impinges on X-Y translation mirror optics 10, where beam 96 is translated or shifted independently along each of two orthogonal translation axes as governed by beam translation controller 93. Controller 93 is typically a processor programmed with a predetermined set of two-dimensional translations or shifts of beam 96 depending on the particular ophthalmic procedure being performed. Each of the X and Y axes of translation is independently controlled, as will be detailed in the following.

An exemplary embodiment of the present invention 10 is for use with a treatment laser 91 comprising a 193-nanometer wavelength excimer laser used in an ophthalmic procedure performed on a workpiece, e.g., an eye 97. However, it is to be understood that the method and system of the present invention will apply equally well to workpieces other than an eye, and further to other light sources.

The translation system 10 (FIGS. 2A–4B) in a preferred embodiment comprises a two-sided device containing four mirrors 11–14, two of which 11,14 are translatable for achieving X-Y translation of an incoming beam 96, retaining parallelism in the outgoing beam 96'. That which will be referred to as the "front" side of the device 10 supports the first mirror 11; that which will be referred to as the "rear" side of the device 10 supports the second, third, and fourth mirrors 12–14. It will be obvious to one of skill in the art that the directionality of the light beam is not important, and that the incoming and outgoing beams could be reversed.

The two sides of the device 10 each have a fixed (relative to the device 10) base 15,16 that is affixed to an upwardly extending plate 17 having a hole 18 therethrough from a front face 19 through to a rear face 20 opposed to the front face 19. The plate's front face 19 is positioned adjacent a rear edge 21 of the first base 15, and the plate's rear face 20 is positioned adjacent a front edge 22 of the second base 16.

Each side further has a translatable mirror mount, here comprising a first 23 and a fourth 24 mirror mount, each of which comprises means for affixing a mirror 11,14 thereto. A second 25 and a third 26 fixed mirror mount are affixed to the second base 16 and have means for affixing the second 12 and the third 13 mirror thereto.

The relative positioning of the four mirror mounts permits the first mirror 11 to receive incoming light 96 from a direction generally perpendicular to a longitudinal axis 27 of the hole 18, which is illustrated herein as horizontal, and to reflect a light beam generally horizontally through the hole 18. The second mirror mount 25 is positioned to permit the second mirror 12 to receive the light reflected generally horizontally from the first mirror 11 through the hole 18 and to reflect light generally horizontally and perpendicular to the light received from the first mirror 11. The third mirror mount 26 is positioned to permit the third mirror 13 to receive the light reflected generally horizontally from the second mirror 12 and to reflect light generally downward, generally perpendicular to the light received from the second mirror 12. The fourth mirror mount 24 is positioned to permit the fourth mirror 14 to receive the downwardly reflected light from the third mirror 13 and to reflect light generally horizontally to form an outgoing beam 96' in a direction generally parallel to the incoming light 96.

Translation of the movable mirror mounts 23,24 is accomplished using a first 27 and a second 28 arm assembly on the front side and a third 29 and a fourth 30 arm assembly on the rear side. All the arm assemblies 27–30 are pivotally attached at one end to their respective base 15,16 and are pivotally attached at an opposing end to the respective translatable mirror mount 23,24. Each arm assembly 27–30 comprises a pair of generally upwardly extending arms connected in generally parallel, spaced-apart relation to each other.

Figure 3A:
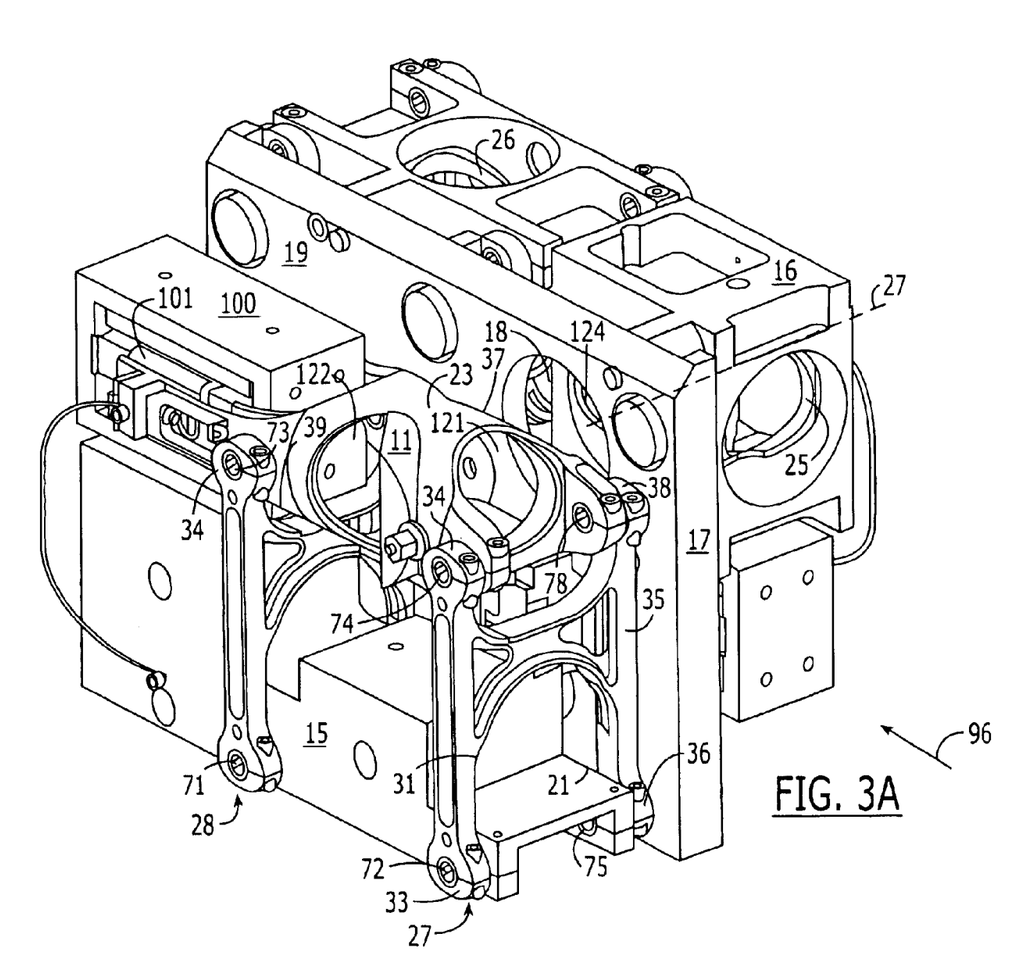
FIGS. 3A and 3B are front-side and rear-side perspective views of the laser translation device.
Figure 4A:
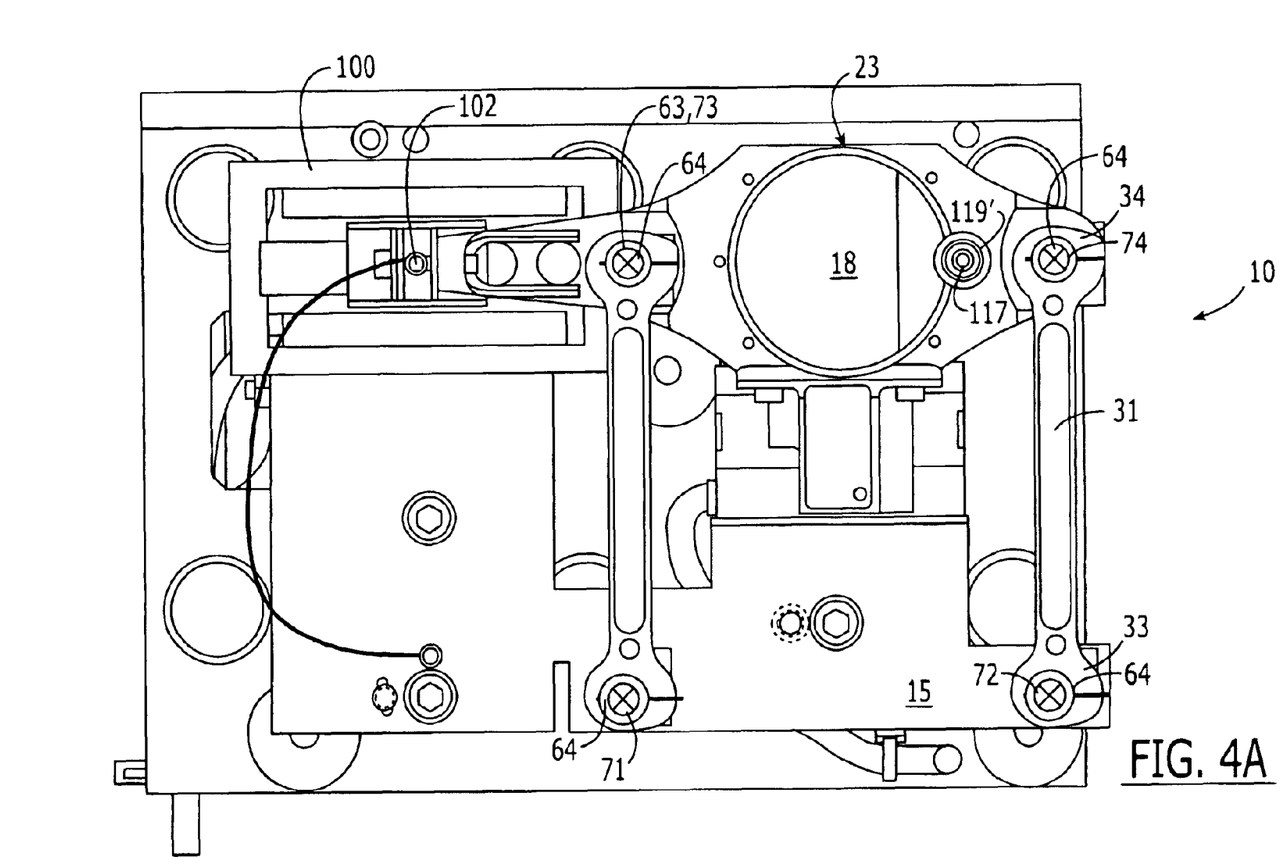
FIGS. 4A and 4B are front and rear schematic views of the laser translation device.

The first 27 and the second 28 arm assemblies are positioned at the front side of the device 10. Each 27,28 has a front arm 31 attached adjacent a front edge 32 of the first base 15 at their lower ends 33 and adjacent a front edge 39 of the first mirror mount 23 at their upper ends 34. Each of the arm assemblies 27,28 further has a rear arm 35 that is attached adjacent the rear edge 21 of the first base 15 at their lower ends 36 and adjacent a rear edge 37 of the first mirror mount 23 at their upper ends 38. The respective front 31 and rear 35 arms of the first and second arm assemblies 27,28 are connected to each other via cross-pieces 45 positioned between the respective upper 34,38 and lower 33,36 ends to form a substantially "H"-shaped structure. The first 27 and the second 28 arm assemblies together form a front and a rear pivotable parallelogram-shaped attachment element at a front and a rear of the first base 15 and first mirror mount 23, respectively.

Figure 3B:
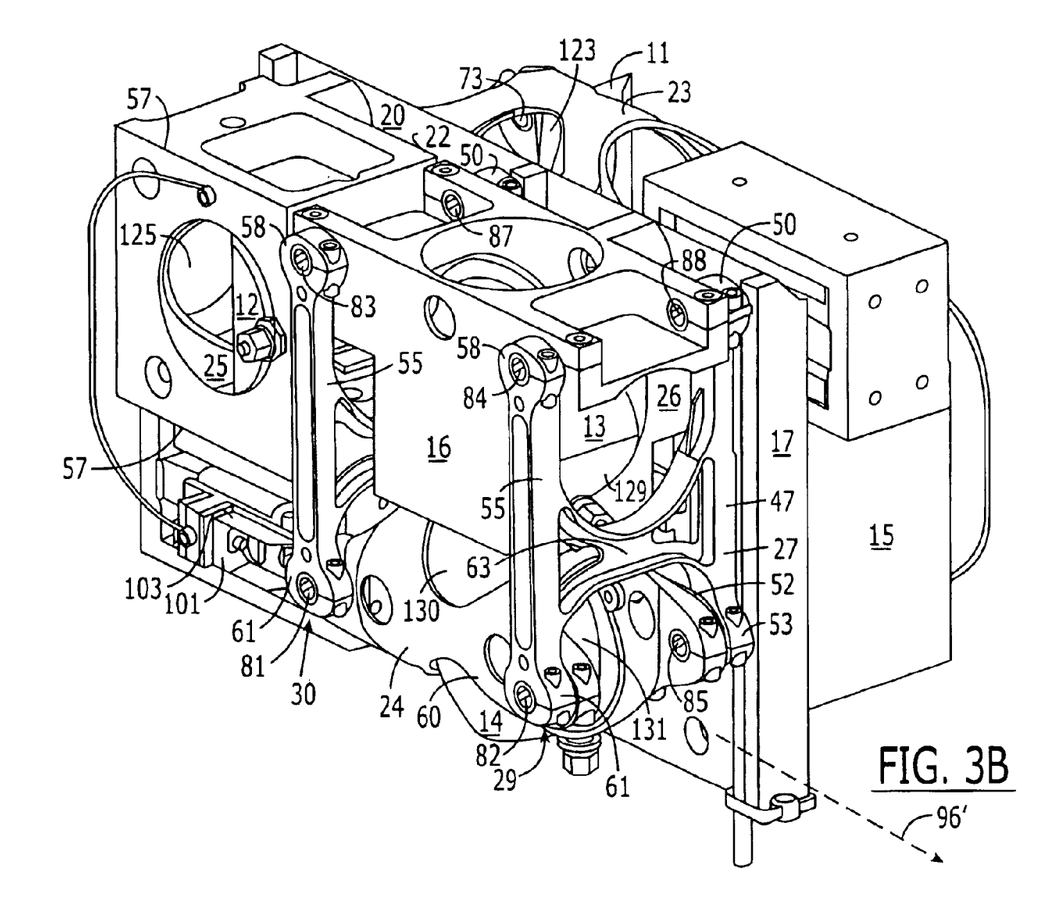
Figure 4B:
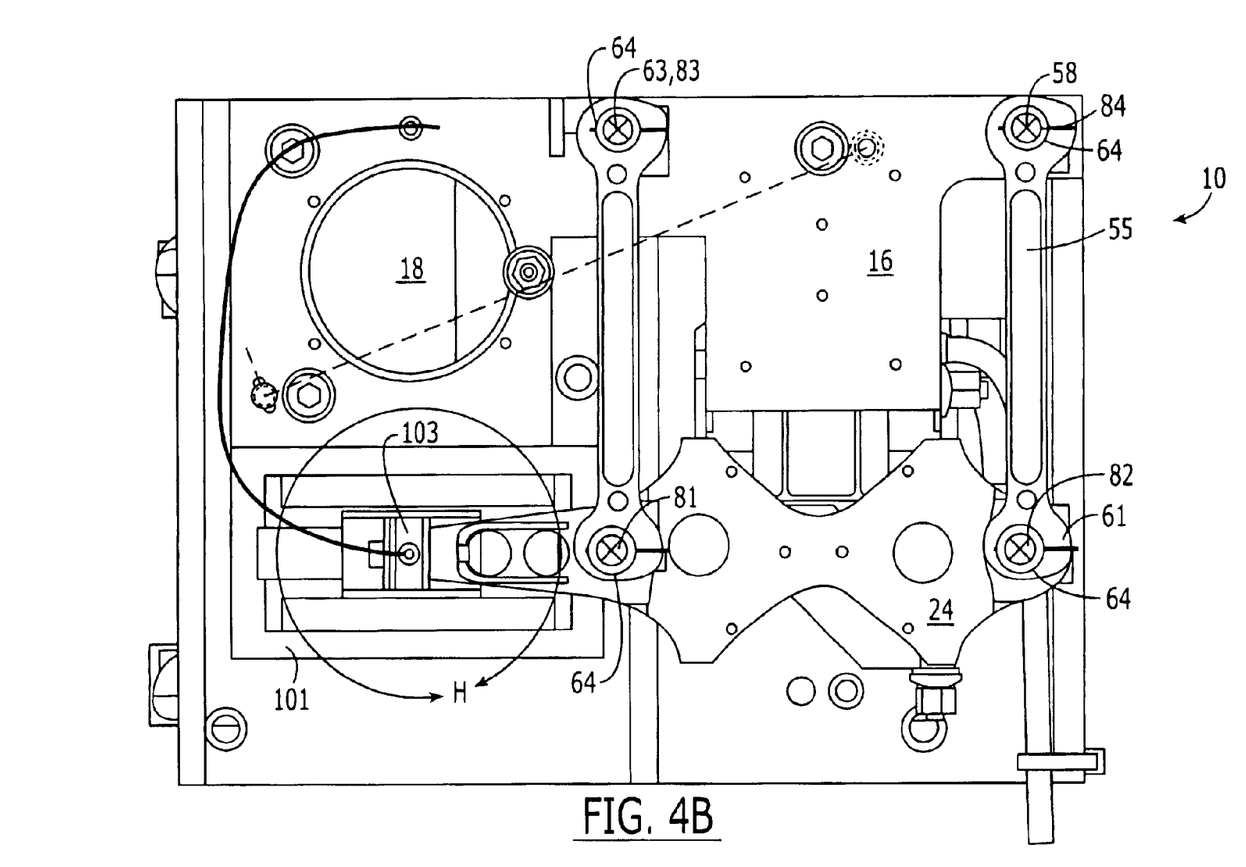
Figure 5:
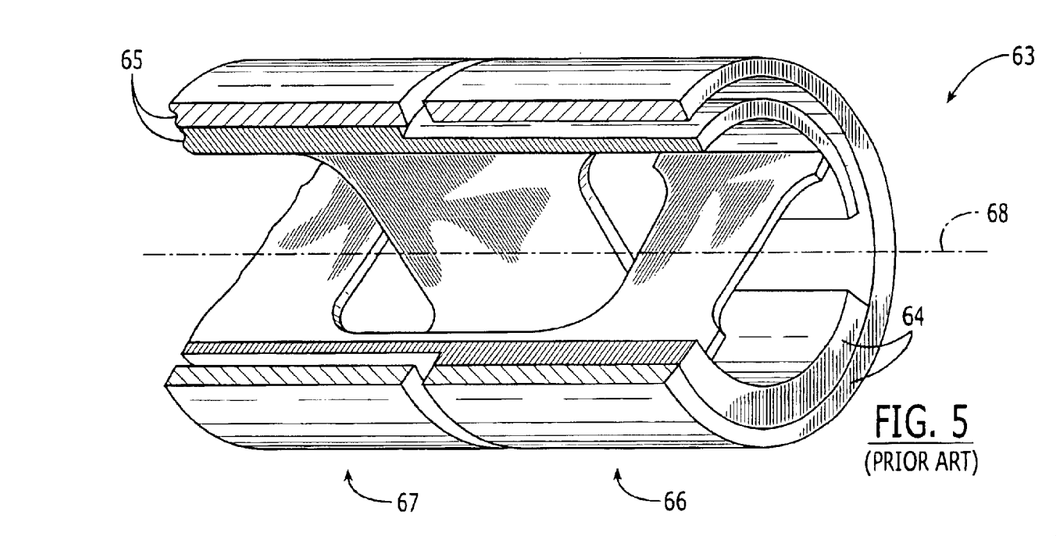
FIG. 5 (prior art) is a partially cutaway perspective view of a flexural pivot.

Similarly, the third 29 and the fourth 30 arm assemblies are positioned at the rear side of the device 10. Each 29,30 has a front arm 47 attached adjacent the front edge 22 of the second base 16 at their upper ends 50 and adjacent a front edge 52 of the fourth mirror mount 24 at their lower ends 53. Each of the arm assemblies 29,30 further has a rear arm 55 that is attached adjacent a rear edge 57 of the second base 16 at their upper ends 58 and adjacent a rear edge 60 of the fourth mirror mount 24 at their lower ends 61. The respective front 47 and rear 55 arms of the third and fourth arm assemblies 29,30 are connected to each other via cross-pieces 63 positioned between the respective upper 50,58 and lower 53,61 ends to form a substantially "H"-shaped structure. The third 29 and the fourth 30 arm assemblies together form a front and a rear pivotable parallelogram-shaped attachment element at a front and a rear of the second base 16 and fourth mirror mount 24, respectively.

The pivotable connections between the bases 15,16 and first and fourth mirror mount 23,24 are provided by two sets of flexural pivots 63, each of which comprises (FIG. 5), for example, a device such as known in the art, as described with reference to FIG. 1 of U.S. Pat. No. 4,405,184, the disclosure of which is incorporated hereinto by reference. It will be noted that each pivot 63 has two "thickened portions" 64,65, one each at a front 66 and a rear 67 section of the pivot 63 (again, "front" and "rear" are used herein to designate positioning relative to the device 10; the pivots 63 are substantially symmetrical). These thickened portions 64,65 are formed by brazing and/or welding the inner half rings to the outer rings on opposite sections, the inner half rings separated from each other, so that the outer rings can rotate with respect to one another. As mentioned above, one disadvantage of these pivots 63 is that, upon pivoting, the two sections are displaced from an original longitudinal axis 68 (termed "runout"), which in turn displaces the elements being connected by the pivot 63 from their original orientations.

Through experimentation, an optimal configuration of two sets of pivots 63 has been found that minimizes such displacement between the bases 15,16 and their respective translatable mirror mounts 23,24 and achieves minimal angular deviation of the mirrors and accuracy, thus optimizing stability. For the front of the device 10, a first set of eight flexural pivots is provided for connecting the first 27 and second 28 arm assemblies with the first base 15 and the first mirror mount 23. A first 71 and a second 72 flexural pivot are positioned at junctions between the lower ends 33 of the front arms 31 and the first base 15 so that the thick portions 64 of a front section 66 thereof are oriented along an outer arc of the pivot 71,72. A third 73 and a fourth 74 flexural pivot are positioned at a junction between the upper ends 34 of the front arms 31 and the first mirror mount 23 so that the thick portions 64 of a front section 66 thereof are oriented along a top arc of the pivot 73,74. A fifth 75 and a sixth (not shown) flexural pivot are positioned at a junction between the lower ends 36 of the rear arms 35 and the first base 15 so that the thick portions 64 of a front section 66 thereof are oriented along an inner arc of the fifth 76 and sixth pivots. A seventh 77 and an eighth 78 flexural pivot are positioned at a junction between the upper ends 38 of the rear arms 35 and the first mirror mount 23 so that the thick portions 64 of a front section 66 thereof are oriented along a bottom arc of the pivot 77,78.

For the rear of the device 10, a second set of eight flexural pivots is provided for connecting the third 29 and fourth 30 arm assemblies with the second base 16 and the fourth mirror mount 24. A first 81 and a second 82 flexural pivot is positioned at a junction between the lower ends 61 of the rear arms 55 and the second base 16 so that the thick portions 64 of a front section 66 thereof are oriented along a top arc of the pivot 81,82. A third 83 and a fourth 84 flexural pivot are positioned at a junction between the upper ends 58 of the rear arms 55 and the fourth mirror mount 24 so that the thick portions 64 of a front section 66 thereof are oriented along an inner arc of the pivot 83,84. A fifth 85 and a sixth (not shown) flexural pivot are positioned at a junction between the lower ends 53 of the front arms 47 and the second base 16 so that the thick portions 64 of a front section 66 thereof are oriented along a lower arc of the fifth 85 and sixth pivots. A seventh 87 and an eighth 88 flexural pivot are positioned at a junction between the upper ends 50 of the front arms 47 and the fourth mirror mount 24 so that the thick portions 64 of a front section 66 thereof are oriented along an outer arc of the pivot 87,88.

Experimentation has shown the above-detailed orientation of the pivots 71–78 to achieve optimal stability by minimizing runout. However, one of skill in the art will recognize that other configurations may be envisioned that will provide improved stability over a purely random orientation of pivots 63, for example, a mirror image of the above or a 90° shift of all pivots 63. Thus the invention is intended to encompass all symmetrical pivot orientations that cancel out the center shift experienced by the pivots upon rotation thereof.

Each side of the device 10 further includes means for translating the translatable mirror mounts 23,24 in a generally horizontal plane. In a preferred embodiment, the translating means comprises a single-phase motor 100,101 and a linear actuator 102,103, respectively, driven by the motor 100,101. Translating the first mirror mount 23 effects a horizontal displacement of the beam; translating the fourth mirror mount 24 effects a vertical displacement of the beam.

Another feature of the device 10 is the mirror mounting element, which is designed to retain a mirror having a planar reflective surface in a desired orientation without imposing bending stress on the mirror sufficient to cause the reflective surface to substantially depart from planarity. Each of the mirror mounting elements incorporated into the mirror mounts 23–26 is substantially the same, with the orientation of the elements altered to support each of the mirrors 11–14 in a desired orientation; therefore, only the first mirror mount 23 will be described in detail.

Figure 6:
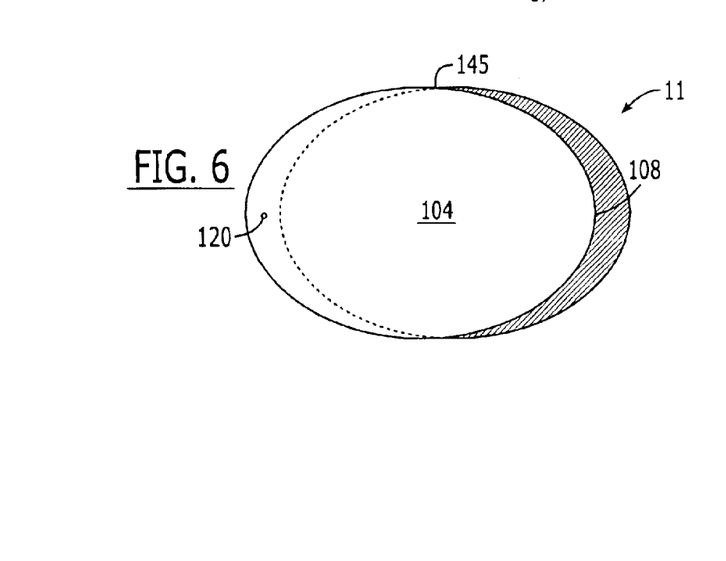
FIG. 6 is a top plan view of the reflective side of the mirror.
Figure 7:
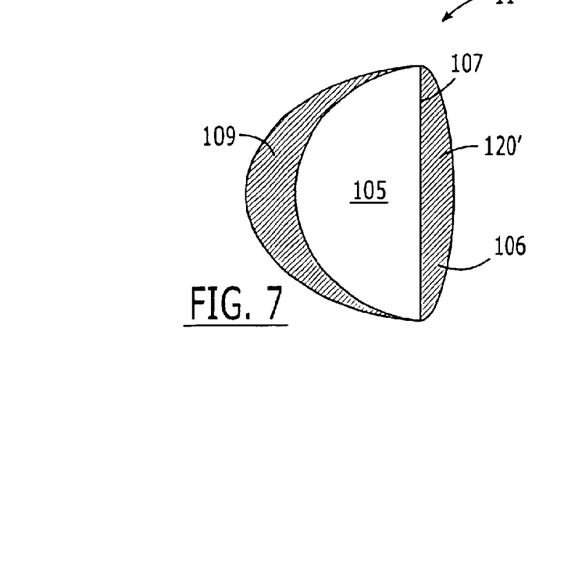
FIG. 7 is a top plan view of the nonreflective side of the mirror.
Figure 8:
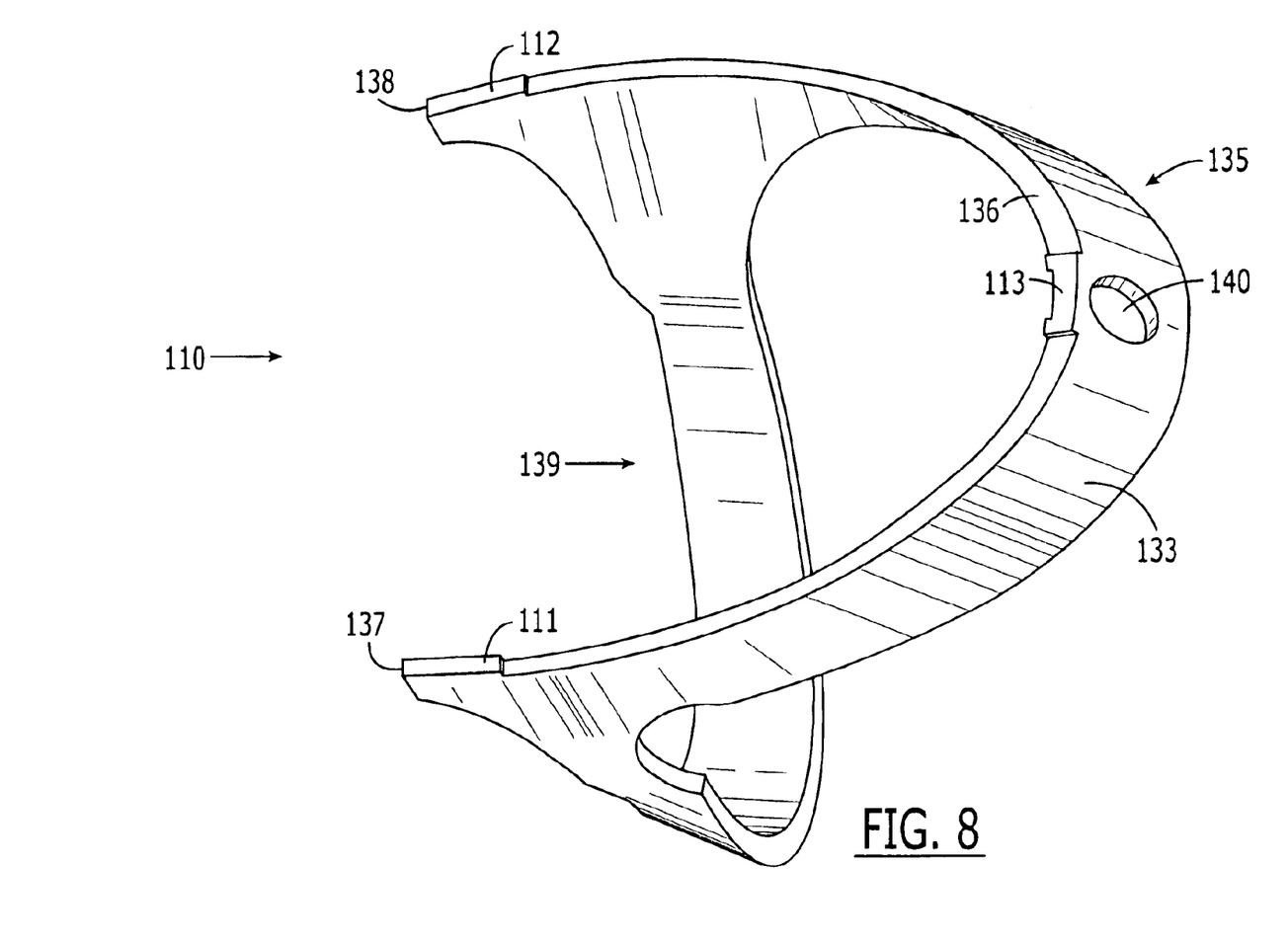
FIG. 8 is a perspective view of the first bracket.

The mirror mount 23 is adapted for supporting and permitting easy replacement of the mirror 11, which for a particular application comprises a planar reflective first surface 104 and a planar nonreflective second surface 105 opposed to the first surface 104 (FIGS. 6 and 7). The first surface 104 is substantially elliptical; the second surface 105 is a truncated ellipse, terminating at the rear in a substantially planar rear face 106 extending from a substantially linear rear edge 107 to a section of arc 108 along the rear of the first surface 104. The first 104 and second 105 surfaces are displaced longitudinally (i.e., along the major axes) from one another, with the front edge of the first surface 104 forward of the front edge of the second surface 105. A front face, or edge, 109 extends in a rearward direction from the front edge of the first surface 104 to the front edge of the second surface 105. The first surface 104 is at an angle of approximately 45° to the front face 109.

The mirror mount 23 for supporting such a mirror 11 comprises a first 110 and a second 114 ring-like bracket affixed within a mirror mount base that in the present embodiment comprises a generally cylindrical housing in the mirror mount 23. The first bracket 110 (FIG. 8) has three generally coplanar pads 111–113 thereon for supporting the reflective side 104 of the mirror 11 thereagainst. A second bracket 114 (FIG. 9) has two surfaces 115,116 in a plane generally parallel with the first bracket pads 111–113 for supporting the front face 109 of the mirror 11 thereagainst. The surfaces 115,116 each comprise a concave, substantially cylindrical section for supporting front face 109. Each of the two surfaces 115,116 is generally opposite a respective one of the pads 111,112. These pairs 115,111;116,112 are oriented on opposite sides of the mirror 11, and also on diametrically opposite sides of the housing 23. Further, these pairs 115,111;116,112 operate to retain the mirror 11 in spaced relation from the mirror mount 23.

A removable mounting screw 117 extends through the mirror mount 23. A pair of washers are dimensioned to admit the mounting screw 117 and are positionable generally opposite the third pad 113 against an outside wall 118 of the mirror mount 23. In a preferred embodiment, the washers comprise a deformable, e.g., rubber, washer 119 and a metal, e.g., aluminum, washer 119', with the deformable washer 119 positioned against the wall 118 and the metal washer 119' positioned against the screw head. The deformable washer 119 is positioned in opposition to the third pad 113. The deformable washer 119 meets the first mirror surface 104 at a point 120 at the rear terminus of a major axis thereof. The opposing pad 113 supports a point 120' opposite the point 120 on the rear face 106 of the mirror 11. This arrangement retains the mirror 11 in contact with the pads 111–113 and the surfaces 115,116 in a predetermined orientation, and removably retains the mirror 11 within the mirror mount 23 without imposing significant bending stress on the mirror 11.

Figure 2A:
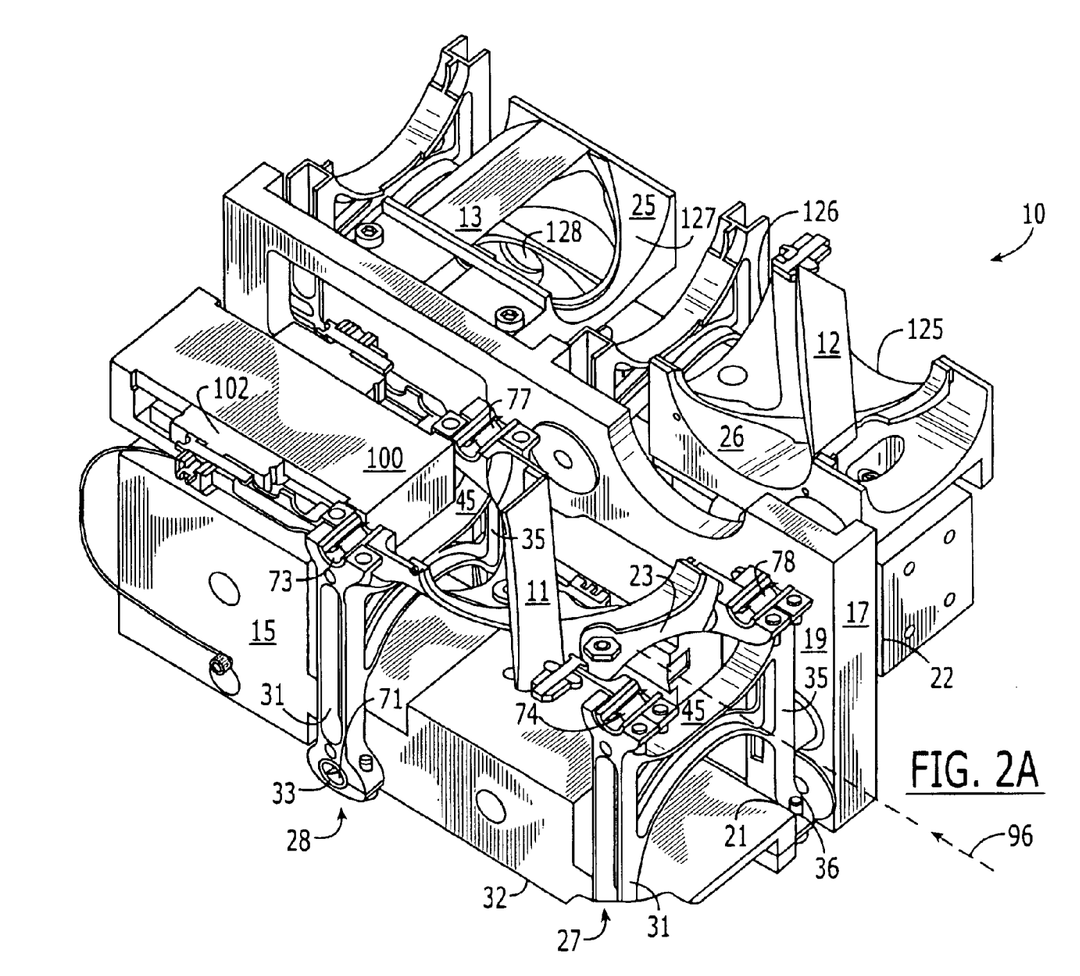
FIGS. 2A and 2B illustrate front-side and rear-side cutaway perspective views of the device, illustrating the optical arrangement of mirrors used to produce translational shifts in a light beam along two axes.
Figure 2B:
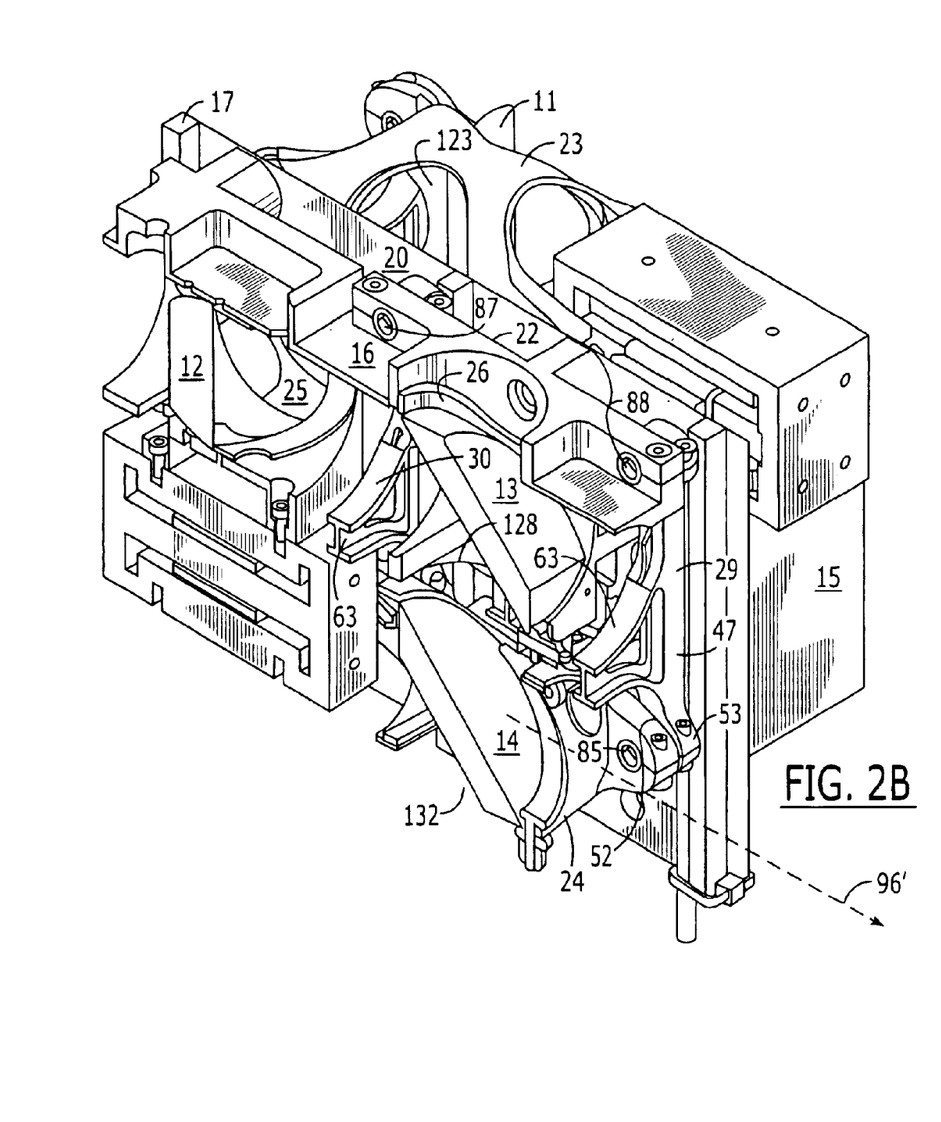

In order to achieve the desired mirror orientations, the first 23 and the second 24 mirror mounts are oriented to position the first 11 and the second 12 mirrors with the reflective surface 104 in a generally vertical plane and thereby parallel to each other, and also at an angle of approximately 45 degrees to the plate 17 (see FIG. 2A). The third 25 and the fourth 26 mirror mounts are oriented to position the third 13 and the fourth 14 mirrors with the reflective surfaces 104 parallel to each other and off-axis from the vertical plane 17 by approximately 45 degrees (see FIG. 2B). Further, the third mirror mount 25 is adapted to orient the third mirror's 13 reflective surface 104 approximately normal to the plate 17 and at an angle of approximately 45 degrees to the second mirror's 12 reflective surface 104.

In order to permit light to pass through the device 10 and contact the mirrors 11–14 as desired, and also to permit access to the mirrors 11–14 for the purpose of ease of replacement, for example, in the field, a plurality of apertures are formed in the mirror mounts 23–26. An incoming beam aperture 121 is positioned to permit light to enter the first mirror mount 23 and impinge on the first mirror 11. A first access aperture 122 permits replacement of the first mirror 11. A first reflective aperture 123 permits light reflected from the first mirror 11 to pass through the plate's hole 18. Light from the first mirror 11 enters the second mirror mount 25 via aperture 124. The second mirror 12 is replaced via second access aperture 125, and exiting light passes through aperture 126 and into aperture 127 leading to the third mirror mount 26. Light from the third mirror 13 exits via aperture 128, and third mirror 13 is replaced via third access aperture 129. Light entering the fourth mirror mount 24 passes through aperture 130 and exits via aperture 131. The fourth mirror 14 is replaced via fourth access aperture 132.

The first 110 and second 114 mounting brackets (FIGS. 8 and 9) are similarly constructed to permit light to pass thereby and therethrough, each comprising a folded ring-like structure. The first bracket 110 comprises a cylinder section having an outer face 133 dimensioned to contact the inner face 134 of the mirror mount 23. A first section 135 of the first bracket 110 has an edge 136 is substantially planar, with the exception of the outwardly extending pads 111–113. The edge 136 terminates in the first 111 and the second 112 pads at opposing points 137,138. A second section 139 of the first bracket 110 extends approximately normal to the first section 135 from the points 137,138, and serves to support the first section 135 when force is applied thereto. Thus the "folding point" of the ring occurs at the opposing points 137,138. A hole 140 is positioned adjacent the third pad 113 for admitting the mounting screw 117.

Figure 9:
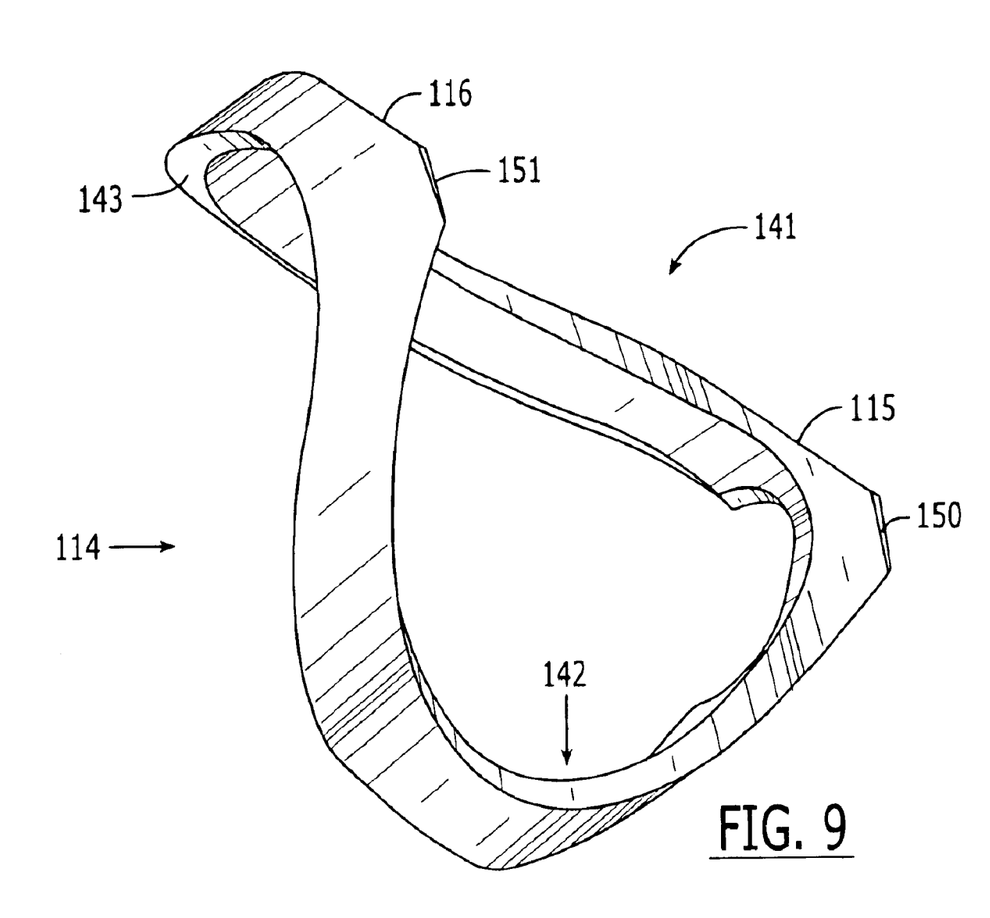
FIG. 9 is a perspective view of the second bracket.

The second bracket 112 is "folded" about the two points 150,151, with a first section 141 and a second section 142 meeting at an oblique angle, and having an outer face 143 dimensioned to contact the inner face 134 of the mirror mount 23.

Figure 10:
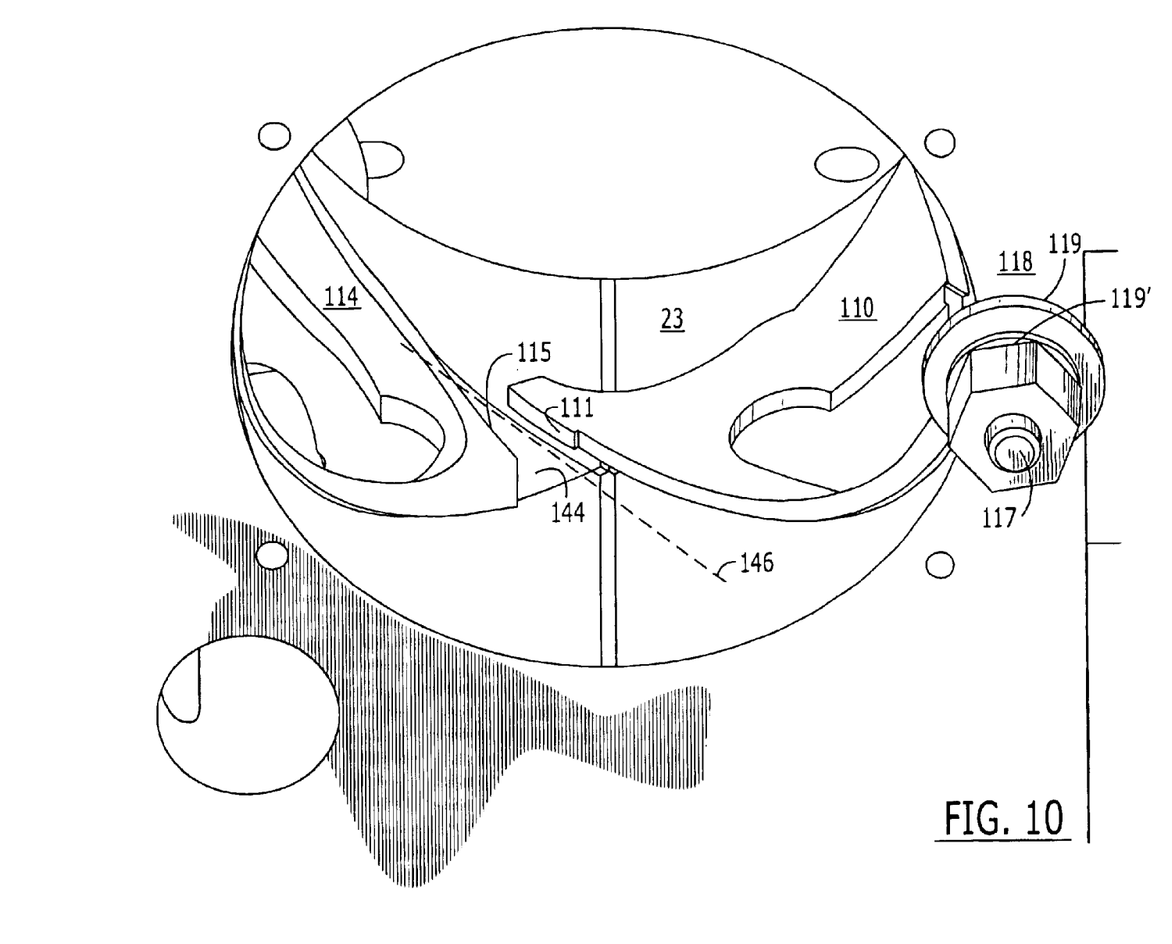
FIG. 10 is a perspective view of the first access aperture and first and second brackets.

In addition to the support provided by the opposing pads 111–113, surfaces 115,116, and washer 119, a slot 144 is formed by the juxtaposing of the first 111 and second 112 brackets. FIG. 10 illustrates the bottom of the first mirror mount 23. It can be seen that the configuration of the first 110 and the second 114 brackets forms the slot 144 between the first pad 111 and the first surface 115 into which the lower edge 145 of the first mirror 11 (FIG. 6) can slide, without, however, contacting the first mirror mount 23, being suspended in spaced relation therefrom by the cooperation of the respective pad/surface pairs 115,111;116,112. Note that the orientation of the slot 144, shown by dotted line 146, defines the verticality of the reflective surface 104 and also the 45 degree angle with the plate 117.

Although the invention has been described relative to a specific embodiment thereof, there are numerous variations and modifications that will be readily apparent to those skilled in the art in the light of the above teachings. It is therefore to be understood that, within the scope of the appended claims, the invention may be practiced other than as specifically described.

What is claimed is:

1. A light beam translation system comprising:

a fixed base;

a translatable mirror mount having means for affixing a mirror thereto;

a first and a second arm assembly pivotally attached at lower ends to the base and pivotally attached at upper ends to the mirror mount, each arm assembly comprising a pair of generally upwardly extending arms connected in generally parallel, spaced-apart relation, a front arm attached adjacent a front edge of the base and the mirror mount and a rear arm attached adjacent a rear edge of the base and the mirror mount, the first and the second arm assemblies thereby forming a front and a rear parallelogram-shaped attachment element at a front and a rear of the base and mirror mount, respectively;

a first set of eight flexural pivots for providing the pivotal attachments, each flexural pivot having a thick portion oriented for achieving optimal stability, a first and a second flexural pivot positioned at a junction between the lower ends of the front arms and the base so that the thick portions of a front section thereof are oriented along an outer arc of the pivot, a third and a fourth flexural pivot positioned at a junction between the upper ends of the front arms and the mirror mount so that the thick portions of a front section thereof are oriented along a top arc of the pivot, a fifth and a sixth flexural pivot positioned at a junction between the lower ends of the rear arms and the base so that the thick portions of a front section thereof are oriented along an outer arc of the pivot, and a seventh and an eighth flexural pivot positioned at a junction between the upper ends of the rear arms and the mirror mount so that the thick portions of a front section thereof are oriented along a top arc of the pivot; and means for translating the mirror mount in a generally horizontal plane.

2. The translation system recited in claim 1, wherein the translating means comprises a single-phase motor and a linear actuator driven by the motor, the actuator affixed in movement-producing relation to the mirror mount.

3. The translation system recited in claim 1, wherein the mirror mount affixing means comprises a bracket for positioning a mirror having a generally planar reflective surface so that the reflective surface is in a generally vertical plane, for translating incoming light in a horizontal plane.

4. The translation system recited in claim 1, wherein the mirror mount affixing means comprises a bracket for positioning a mirror having a generally planar reflective surface so that the reflective surface is in a plane at an angle of approximately 45 degrees to a vertical plane, for translating incoming light in a vertical plane.

5. The translation system recited in claim 1, wherein the mirror mount comprises means for retaining a mirror having a planar reflective surface in a desired orientation without imposing bending stress on the mirror sufficient to cause the reflective surface to substantially depart from planarity.

6. The translation system recited in claim 5, wherein the mirror retaining means comprises:
- a mirror mount base;
- a first bracket affixed to the mirror mount base having three generally coplanar pads thereon for supporting the reflective side of the mirror thereagainst;
- a second bracket affixed to the mirror mount having two surfaces shaped to support an edge of the mirror thereagainst opposed to the reflective side, each of the two surfaces generally opposite a respective one of the pads; and
- a removable mounting screw extending through the mirror mount; and
- a washer dimensioned to admit the mounting screw and positionable generally opposite a third pad against an outside wall of the mirror mount, the washer positioned to retain the mirror in contact with the pads and the surfaces in a predetermined orientation, the pads, the surfaces, and the washer operable to removably retain the mirror within the mirror mount without imposing bending stress on the mirror sufficient to cause the reflective surface to substantially depart from planarity.

7. The translation system recited in claim 6, wherein the first and the second bracket cooperate to retain the mirror in spaced relation from the mirror mount base.

8. The translation system recited in claim 7, wherein the second bracket is shaped to support a nonreflective edge of the mirror, the nonreflective edge meeting the reflective surface at an angle of approximately 45 degrees.

9. The translation system recited in claim 8, wherein the surfaces each comprise a concave, substantially cylindrical section.

10. The translation system recited in claim 8, wherein:
- the first mirror mount affixing means comprises a bracket for positioning a first mirror having a generally planar reflective surface so that the reflective surface is in a generally vertical plane;
- the second mirror mount affixing means comprises a bracket for positioning a second mirror having a generally planar reflective surface so that the reflective surface is in a generally vertical plane; and
- the third and the fourth mirror mount affixing means each comprise a bracket for positioning a third and a fourth mirror having generally planar reflective surfaces so that the reflective surfaces are parallel to each other and off-axis from the vertical plane, movement of the fourth mirror for translating light reflected from the third mirror in a vertical plane.

11. The translation system recited in claim 10, wherein:
- the first and the second mirror mount bracket are adapted to orient the first and the second mirror reflective surfaces at an angle of approximately 45 degrees to the plate; and
- the third mirror mount bracket is adapted to orient the third mirror reflective surface approximately normal to the plate and at an angle of approximately 45 degrees to the second mirror reflective surface and the fourth mirror mount bracket is adapted to orient the fourth mirror reflective surface approximately parallel to the third mirror reflective surface.

12. The translation system recited in claim 1, wherein:
- the base comprises a first base, and further comprising an upwardly extending plate having a hole therethrough from a front face through to a rear face opposed to the front face, the plate front face adjacent a rear edge of the first base, and a second base having a front edge adjacent the plate rear face; wherein:
- the mirror mount comprises a first mirror mount positioned to permit the first mirror to receive incoming light from a direction generally perpendicular to a longitudinal axis of the hole and to reflect a light beam generally horizontally through the hole, and further comprising:
- a second fixed mirror mount and a third fixed mirror mount affixed to the second base and having means for affixing a second and a third mirror thereto, respectively, the second mirror mount positioned to permit the second mirror to receive light reflected generally horizontally from the first mirror through the hole in the plate and to reflect light generally horizontally, the third mirror mount positioned to permit the third mirror to receive light generally horizontally from the second mirror and to reflect light generally downward;
- a fourth translatable mirror mount having means for affixing a fourth mirror thereto, the fourth mirror mount positioned to permit the fourth mirror to receive downwardly reflected light from the third mirror and to reflect light generally horizontally in a direction generally parallel to the incoming light;
- a third and a fourth arm assembly pivotally attached at upper ends to the second base and pivotally attached at lower ends to the fourth mirror mount, each of the third and the fourth arm assembly comprising a pair of generally upwardly extending arms connected in generally parallel, spaced-apart relation, a rear arm attached adjacent a rear edge of the second base and of the fourth mirror mount, and a front arm attached adjacent a front edge of the second base and of the fourth mirror mount, the first and the second arm assemblies thereby forming a front and a rear parallelogram-shaped attachment element at a front and a rear of the second base and the fourth mirror mount, respectively;
- a second set of eight flexural pivots for providing the pivotal attachments, each flexural pivot having a thick portion oriented for achieving optimal precision, a first and a second flexural pivot positioned at a junction between the lower ends of the rear arms of the third and the fourth arm assemblies and the second base so that the thick portions of a rear section thereof are oriented along an lower arc of the pivot, a third and a fourth flexural pivot positioned at a junction between the upper ends of the rear arms of the third and the fourth arm assemblies and the fourth mirror mount so that the thick portions of a rear section thereof are oriented along an outer arc of the pivot, a fifth and a sixth flexural pivot positioned at a junction between the lower ends of the front arms and the second base so that the thick portions of a front section thereof are oriented along a lower arc of the pivot, and a seventh and an eighth flexural pivot positioned at a junction between the upper ends of the front arms of the third and the fourth arm assemblies and the fourth mirror mount so that the thick portions of a front section thereof are oriented along an outer arc of the pivot; and
- means for translating the fourth mirror mount in a generally horizontal plane.

* * * * *